United States Patent [19]

Rosback, deceased et al.

[11] 4,283,587
[45] Aug. 11, 1981

[54] ADSORPTIVE SEPARATION OF AROMATIC ISOMERS

[75] Inventors: Donald H. Rosback, deceased, late of Elmhurst, Ill.; by Janice M. Gillespie, executrix, Bartlett, Ill.

[73] Assignee: UOP Inc., Des Plaines, Ill.

[21] Appl. No.: 160,053

[22] Filed: Jun. 16, 1980

[51] Int. Cl.³ .............................................. C07C 7/13
[52] U.S. Cl. .................................. 585/828; 208/310 Z
[58] Field of Search ..................... 585/828; 208/310 Z

[56] References Cited

U.S. PATENT DOCUMENTS

| | | | |
|---|---|---|---|
| 2,930,447 | 3/1960 | Barrer | 55/66 |
| 3,558,732 | 1/1971 | Neuzil | 585/828 |
| 3,686,342 | 8/1972 | Neuzil | 585/828 |
| 3,804,746 | 4/1974 | Chu | 585/828 |
| 3,855,333 | 12/1974 | Neuzil | 585/828 |
| 4,079,094 | 3/1978 | Rosback et al. | 585/828 |

*Primary Examiner*—O. R. Veritz
*Assistant Examiner*—Wayne A. Langel
*Attorney, Agent, or Firm*—James R. Hoatson, Jr.; Louis A. Morris; William H. Page II

[57] ABSTRACT

An adsorptive separation process is disclosed for separating para-aromatic isomers from a hydrocarbon feed containing a mixture of aromatic isomers, using a crystalline aluminosilicate adsorbent which has been treated with an alkyl amine preferably an alkyl amine hydrochloride. The alkyl amine treatment substantially increases the selectivity of the adsorbent for the para-xylene isomer, relative to the heavy desorbent p-DEB, thereby improving the efficiency of the separation process.

8 Claims, No Drawings

ADSORPTIVE SEPARATION OF AROMATIC ISOMERS

BACKGROUND OF THE INVENTION

This application relates to the separation of aromatic hydrocarbon isomers by selective adsorption on a solid crystalline aluminosilicate adsorbent which has been treated with an alkyl amine hydrochloride. The selectively adsorbed para-isomer is removed from the adsorbent with a suitable desorbent.

DESCRIPTION OF THE PRIOR ART

It is well known that crystalline aluminosilicates can be used to resolve hydrocarbon mixtures. In aromatic hydrocarbon separation, and especially in separating the $C_8$ aromatic isomers, it is known that adding selected cations at the zeolite cationic sites enhances the selectivity of the zeolite for a given aromatic isomer. Examples of specific adsorbents and more details about this process may be found in U.S. Pat. Nos. 3,558,732 and 3,686,342 (both in Cl. 260-674), the teachings of which are incorporated by reference.

The adsorbed isomer, which is usually the para-isomer, is usually removed from the adsorbent with a desorbent. Such a desorbent must be capable of desorbing the adsorbed isomer without requiring large mass flow rates and must also be easily displaced from the adsorbent during a subsequent adsorption cycle. Additionally the desorbent must be easily separable from both adsorbed and nonadsorbed feed components to permit the recovery of high purity product streams and to permit the reuse of desorbent. Since this separation is generally done by fractionation, it is preferred that the boiling point difference between the feed and desorbent be sufficiently great to permit separation of feed components from desorbent economically by simple fractionation.

In the separation of $C_8$ aromatic isomers, both toluene and diethylbenzene may be used as desorbents provided that the sieve is tailored to the desorbent. Toluene units were designed for a feed substantially free of $C_8$ naphthenes. Such a feed could be obtained as a fraction of a reformate, perhaps after solvent extraction and extractive distillation had been used to purify it. These units work well but with the great increase in energy costs which has occurred in recent years, they have become less economical to operate. Fractionation is used to separate desorbent from feed components. Reflux is required in fractionation, so it is necessary to vaporize and condense vast amounts of desorbent. If the desorbent were a relatively heavy material, and remained as a liquid in the bottoms of a fractionator, it would only be necessary to vaporize and condense feed components, which comprise a smaller fraction of fractionator throughput than the desorbent. For this reason, namely utility costs of operating fractionators, the use of heavy desorbents is now preferred in aromatic separation units. It is not possible, in an existing unit, to simply replace the light desorbent with a heavy desorbent because the adsorbents which give good performance with a light desorbent do not always work well with a heavy desorbent.

Another factor in the selection of desorbent is the flexibility of operation in a unit. If a toluene desorbent system is used, it is not possible for a refiner to increase production of a desired $C_8$ aromatic isomer by adding a $C_8$ aromatic isomerization unit to isomerize the non-desired $C_8$ aromatic isomers. The $C_8$ aromatic isomerization units commonly used produce a small amount of $C_8$ naphthenes which accumulate in the toluene desorbent and contaminate it.

Accordingly for a number of reasons, it would be highly desirable to alter the operation of existing $C_8$ aromatic separation units which use a toluene desorbent system so that a heavy desorbent could be used. it is not too difficult to modify the fractionators associated with such a unit to permit use of a heavy desorbent, but it is usually prohibitively expensive to replace the adsorbent to permit use of a heavy desorbent. In a typical commercial unit, 100,000 to 300,000 kilograms of adsorbent are in place, and it is expensive to remove this material and replace it with another adsorbent which would be amenable to the heavy desorbent. It would be desirable to modify these existing adsorbents, characterized by low barium and high potassium contents, to permit use of a heavy desorbent.

It would also be desirable to have an in situ adsorbent treatment which would increase an adsorbent's effective capacity for the $C_8$ para-isomer, by increasing the selectivity for the desired para-isomer. Such a sieve treatment would permit an increase in the capacity of the unit while simultaneously permitting an increase in product purity, with savings in utility costs as well.

Several modifications of adsorbents have been proposed in the art. U.S. Pat. No. 3,855,333 (Cl. 260-674A), the teachings of which are incorporated by reference, discloses that adding an alcohol substrate to the adsorbent improves an aromatic separation process. The addition of alcohol to the adsorbent permitted a benzene desorbent to be used, avoiding the problem of contamination of toluene desorbent with $C_8$ naphthenes.

In U.S. Pat. No. 3,840,610 (Cl. 260-674SA), it is disclosed that operation with an Na-Y zeolite adsorbent which contained about 12 wt.% water resulted in an improved process.

In U.S. Pat. No. 3,698,157 (Cl. 55-67), it is disclosed that operation of a $C_8$ aromatic separation process can be improved by using as an adsorbent an aluminosilicate zeolite which has been contacted with an organic-radical substituted silane.

In attempting to find a way to modify the performance of Ba-K type X zeolites which used a toluene desorbent system, I could not find anything in the prior art which suggested a way to treat this adsorbent, in situ, to permit its use with a heavy desorbent. I have discovered that treatment of these zeolites with an aqueous alkyl amine hydrochloride followed by washing and drying produces an adsorbent with both increased selectivity for the desired paraisomer, and also with increased aromatic capacity.

SUMMARY OF THE INVENTION

Accordingly the present invention provides a process for separating aromatic hydrocarbons from a feed containing a mixture of aromatic isomers including para-isomers. The process comprises contacting, at adsorption conditions, the feed with a type X or type Y zeolite which has been cation exchanged at exchangeable cationic sites with cations which make the zeolite selective for the paraisomer, to effect the selective adsorption of said para-isomer by said adsorbent. The improvement comprises utilizing a zeolite which has been treated with an alkyl amine hydrochloride or alkyl amines.

DETAILED DESCRIPTION OF THE INVENTION

Feedstocks which can be used in the process of this invention include bi-alkyl substituted mono-cyclic aromatics having from 8 to 18 carbon atoms per molecule. Preferred feedstocks are xylene isomers and ethylbenzene.

The feed stream will always contain one or more extract components and one or more raffinate components. An extract component is one that is selectively adsorbed by the adsorbent, while a raffinate component is one that is less selectively adsorbed. As applied to a process for separating mixtures of para-xylene and other xylenes in ethylbenzene, para-xylene is usually an extract component, at least with the above-mentioned adsorbents, while the other xylene components and ethylbenzene are raffinate components.

Desorbent is any material capable of desorbing an extract component from the adsorbent.

Adsorbents modified by the practice of the present invention may be used in either a single bed, swing bed of two or more beds or preferably in a simulated moving bed countercurrent flow system. An example of such a system is described in U.S. Pat. No. 2,985,589 issued to D. B. Broughton and in a paper entitled "Continuous Adsorptive Processing—A New Separation Technique" by D. B. Broughton presented at the 34th Annual Meeting of the Society of Chemical Engineers at Tokyo, Japan on Apr. 2, 1969.

The adsorbents which can be used in the process of this invention include Type X and Type Y zeolites which have been ion exchanged to contain various cations. The improvements afforded by the present invention are believed to be applicable to any adsorbent which has been used in the past to separate the above-mentioned feedstocks into various isomers. The invention is especially useful when used to modify the characteristic of Type X sieves containing barium or both barium and potassium cations and to modify the characteristics of Type Y sieves containing potassium cations.

The particular type of adsorbent used is not believed critical. The benefits of the present invention have been seen on tests of both X and Y sieves, and on sieves containing only barium, only potassium, or mixtures thereof. A broader discussion of adsorbents which can be used in the process of this invention is included in U.S. Pat. No. 3,734,974 (Cl. 260-674SA, 208-310), the teachings of which are incorporated by reference. Briefly stated, either X or Y zeolites can be used, and they may contain cations selected from the Group I-A, Group II-A and Group IV metals. Barium or potassium or mixtures thereof as cations placed upon the zeolite are preferred. The process of the present invention works especially well with adsorbents comprising Type X zeolites with low barium and high potassium contents, Type X zeolites with high barium and low potassium contents, Type X zeolites completely exchanged with barium and Type Y zeolites completely exchanged with potassium.

Operating conditions contemplated for practicing the process of the present invention are conventional.

A number of important process parameters will now be described. These terms are used in interpreting experimental data hereafter reported.

Selectivity is roughly equivalent to the term relative volatility in distillation. It is an indication of an adsorbent's efficiency at separating different species. For successful commercial separation, a selectivity of at least about 2.0 is preferred. A lower selectivity requires a large inventory of adsorbent to make the separation. High selectivities reduce the adsorbent inventory required.

The retention volume is a qualitative indication of the selectivity between an adsorbed species and the desorbent. As applied to para-xylene recovery, i.e. when para-xylene is the extract or adsorbed phase, the para-xylene retention volume is an indication of how much desorbent is required to desorb para-xylene from the adsorbent. In general, for the test conditions described hereafter, para-xylene retention volume should be between 25 and 30 cc. A value less than about 22 cc means that the selectivity for para-xylene with respect to the desorbent is less than unity, which is undesirable. A value greater than about 35 cc indicates that too much desorbent will be required to desorb the para-xylene.

Para-xylene retention volume is closely related to, but not directly proportional to the selectivity of para-xylene compared to desorbent. A selectivity of para-xylene compared to desorbent of about 1.1 to 1.5 is considered ideal. This means that the desorbent and para-xylene will displace each other equally well. A para-xylene to desorbent selectivity much greater than one is to be avoided, because this means that too much desorbent would be required to displace para-xylene from the adsorbent. A para-xylene to desorbent selectivity, on the other hand, less than one is not advantageous, because although this means that only a small amount of desorbent is required to remove para-xylene from the adsorbent, it is very difficult for the para-xylene to subsequently displace desorbent from the adsorbent when the adsorbent contacts the feed.

Expressed in terms of selectivity, it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically they must not reduce or destroy the critical selectivity of the adsorbent for the extract components with respect to the raffinate components.

Although isothermal, isobaric, liquid phase operation is preferred, it is possible to operate with gradients in pressure, temperature, desorbent concentration, etc. Where the desorbent is used as a dilute stream, e.g., paradiethylbenzene in a heavy paraffin diluent, it may be desirable to use two strengths of this material to economize on the use of paradiethylbenzene desorbent. In a sense, the existing four zone technology provides for a relatively weak desorbent, generated in zone IV, with a stronger desorbent being added as the conventional desorbent stream, with a uniform composition. It is also possible to use a three zone, or a four zone, simulated moving bed process wherein a dilute desorbent is used in one portion of the simulated moving bed, and a more concentrated desorbent is used in another portion. Alternatively, the temperature of the simulated moving bed, or of the streams passing through it, can be changed. For some desorbents, their characteristics change at different temperatures, and it may be desirable to add a first quantity of desorbent at a relatively low temperature, followed by a second quantity of desorbent at a relatively higher temperature. Details of these variations on the simulated moving bed theme are given in U.S. Pat. Nos. 4,029,717 (Cl. 260-674SA), 4,031,151 (Cl. 260-666A), 4,031,155 (Cl. 260-674SA) and 4,031,156 (Cl. 260-674SA), the teachings of which are incorporated by reference.

In most applications, the cost and complexity of operating with different concentrations and/or temperatures of desorbent are not economically justified. I believe that isothermal operation, with concentrated desorbent, is the preferred mode operating a $C_8$ aromatic separation process.

My discovery that treatment of the above sieves with an aqueous alkyl amine hydrochloride followed by washing and drying produced an adsorbent with both increased selectivity for the desired para-isomer, and also with increased aromatic capacity, was surprising because based on some earlier published work, it had been found that adding ammonia derivatives, such as methylamine, to a Type X molecular sieve did not alter selectivity. This was disclosed in U.S. Pat. No. 2,930,447 (Cl. 183-114.2), which showed that it was possible to alter the selectivity for oxygen and nitrogen of chabazite and mordenite by treatment with methylamine. The patent disclosed at column 4, lines 5-35, that adding a non-aqueous non-polar adsorbate on sodium zeolite X did not alter the selectivity. The system studied was the capacity of sodium zeolite X for neopentane or trin-butylamine in the presence of various amounts of benzene.

The alkyl amines are relatively poor ion exchangers, but they do exchange slightly. When only a small amount of, e.g., $MA.H+$ or $DMA.H+$ is needed, the alkyl amine in aqueous solution, generating, for example, $CH_3NH_3^+ + OH^-$, would probably work, but at higher exchange cost. The use of an alkyl amine hydrohalide significantly speeds up the ion exchange process, with an alkyl amine hydrochloride being especially preferred.

The alkyl amine hydrochloride can be any one which can interact with the zeolite adsorbent. There is an actual exchange which occurs between the zeolite and the alkyl amine hydrochloride. The nature of the interaction between the alkyl amine hydrochloride and the zeolite is understood at this time to be as shown below:

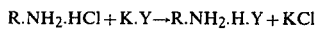

$$R.NH_2.HCl + K.Y \rightarrow R.NH_2.H.Y + KCl$$

Based on experimental results available to date, it is believed that use of a relatively short chain alkyl group, preferably a methyl group, is the most desirable form of alkyl amine hydrochloride. It is believed this is due to more complete exchange which occurs with the lighter compound, methylamine hydrochloride, than occurs with the heavier compound, dimethylamine hydrochloride. It is possible that for a given percentage exchange, both would act the same way. The effect of the alkyl amine hydrochloride differs depending on the type and amount of other cations on the sieves, and on the nature of the molecular sieve.

In all cases tested, Type Y sieves with potassium, Type X with barium, and Type X with mixtures of barium and potassium, the selectivities for paraxylene/ethylbenzene improved with use of the adsorbent of my invention. Similarly, in all cases tested, the paraxylene/p-DEB selectivity improved.

EXAMPLE I: ADSORBENT PREPARATION

Four basic adsorbents were tested. These adsorbents had the following properties.

Adsorbent A: 22.1% barium oxide, 6.1% potassium oxide, X faujasite,
Adsorbent B: 25.1% barium oxide, 3.1% potassium oxide, X faujasite,
Adsorbent C: 31.5% barium oxide, X faujasite, and
Adsorbent D: 15.8% potassium oxide, Y faujasite.

Desorbent A is a relatively low barium, high potassium adsorbent which works very well for separation of para-xylene from mixed xylene isomers, when a toluene desorbent is used. Adsorbents B (a relatively high barium, low potassium, Type X faujasite), C (a high barium, Type X faujasite) and D (a high potassium, Type Y faujasite) are all sieves which are selected for paraxylene and function very well even when para-diethylbenzene desorbent is used.

The initial preparation of these materials was by the following conventional ion exchange techniques, and forms no part of the present invention.

A good laboratory method of preparing any of the above adsorbents is to place, e.g. Na form Type X zeolite purchased from Linde, in a column, e.g., a length of glass tubing. The first step in the ion exchange process is to prewet the adsorbent with pretreated water. This should be done slowly and with some care, because there is a large heat of adsorption. Depending on the exact source of the zeolite material, it may be desirable to give a mild caustic washing step to remove acidity and excess silica. When such a step is desired, it may be accomplished by contacting the sieves with 0.25 wt.% NaOH solution, in an amount equivalent to 0.0335 kilograms NaOH/kilograms of dry zeolite, followed by water washing and a gentle drying treatment. It may be advantageous to calcine the zeolites at this point, but it does not appear necessary. After the adsorbent is immersed in water, the ion exchange solution can be added at the following conditions: 60° C. column temperature, upflow, LHSV of 2, and use of an aqueous solution of desired cation, e.g., one containing 0.32 wt.% $Ba^{++}$ ions. A good way to form this solution is to add $BaCl_2$ to water. To avoid concentration gradients in the adsorbent, it is preferred, after the desired amount of barium has been added, to "polish" the zeolite by recycling material from one end of the column to the other for several hours. If it is desired to add a second cation, a second ion exchange can be performed.

When $K+$ ions are desired on the zeolite, a solution containing 0.35 wt.% potassium can be prepared using KCl as the potassium source and following the exchange instructions above, substituting potassium for barium.

The zeolite, once exchanged, may be washed for several hours with water, then dried.

The adsorbent of my invention was then prepared by contacting the above adsorbents with an alkyl amine hydrochloride in the following manner. A 0.22 M solution of an alkyl amine hydrochloride was recycled over an appropriate volume of adsorbent at 60° C. for 6 hours. The adsorbent was washed free of chloride ions and then dried.

An analysis of the adsorbent was obtained by analyzing the liquid left over after exchange with alkyl amine hydrochloride. Some of the adsorbent was also analyzed for percent carbon and percent nitrogen by conventional techniques. The results of these analyses follow as Table I.

TABLE I

Carbon-Nitrogen Analysis of Exchanged Sieves With Calculated Equivalents of Alkyl Amines Added to Sieve by Exchange Compared With Inorganic Ions Removed

| ADSORBENT | A | B | C | D |
|---|---|---|---|---|
| Methylamine Hydrochloride Exchange | | | | |
| % C | 0.35 | 0.31 | 0.21 | 1.03 |
| % $NH_3$ | 0.48 | 0.37 | 0.29 | 1.52 |
| C/N Mole Ratio | 1.03 | 1.19 | 1.03 | 1.04 |
| MA . H Equiv. Added | 0.051 | 0.040 | 0.032 | 0.121 |
| Ba, K, Na Equiv. Removed | 0.050 | 0.039 | 0.035 | 0.116 |
| Dimethylamine Hydrochloride Exchange | | | | |
| % C | 0.07 | 0.14 | 0.06 | 1.31 |
| % $NH_3$ | 0.16 | 0.10 | 0.04 | 1.01 |
| C/N Mole Ratio | 0.62 | 1.98 | 2.13 | 1.84 |
| DMA . H Equiv. Added | 0.017 | 0.011 | 0.004 | 0.080 |
| Ba, K, Na Equiv. Removed | 0.025 | 0.020 | 0.013 | 0.071 |

The ion equivalents removed by exchanging the sieves with the two alkyl amine hydrochlorides tested are presented in the following table, Table II.

TABLE II

| ADSORBENT | A | B | C | D |
|---|---|---|---|---|
| Methylamine Hydrochloride Exchange | | | | |
| Ba | 0.004 | 0.016 | 0.033 | — |
| Na | 0.001 | 0.002 | 0.002 | 0.001 |
| K | 0.045 | 0.021 | — | 0.115 |
| ε of Equiv. Removed | 0.050 | 0.039 | 0.035 | 0.116 |
| Dimethylamine Hydrochloride Exchange | | | | |
| Ba | 0.001 | 0.002 | 0.012 | — |
| Na | 0.001 | 0.001 | 0.001 | 0.001 |
| K | 0.023 | 0.017 | — | 0.074 |
| ε of Equiv. Removed | 0.025 | 0.020 | 0.013 | 0.075 |

Where only a little ion exchange occurred using dimethylamine hydrochloride, especially in the examples on the Type X sieves, namely Adsorbents A, B and C the analytical method is being pushed to the limits of its reliability. This is because the amount of exchange is calculated from analysis of the spent impregnating solutions. Large volumes of solution, containing trace amounts of ions, are difficult to analyze. The analytical method works much better as applied to the potassium-Y adsorbent, Adsorbent D, because in that case, greater amounts of cations and methylamine hydrochloride were exchanged.

Table II also illustrates that the alkyl amine hydrochlorides removed potassium preferentially. Barium is next in preference, proportional to the amount of barium originally present.

The C-N mole ratios shown in Table I are supporting evidence for the presence of MA.H+ and DMA.H+ on the adsorbent. The adsorbent has about 0.05% chloride, dry basis.

The above would indicate the following possible exchange for the D adsorbent.

$$CH_3.NH_2.HCl(aq) + D \rightarrow CH_3.NH_2.H\text{-}D + KCl(aq)$$

EXAMPLE II: SELECTIVITY TESTS

These adsorbents, after ion exchange as outlined above, were tested to determine the effect of the alkyl amine hydrochloride on Adsorbent A. The test method used was equivalent to that described in U.S. Pat. No. 3,734,974, the teachings of which are incorporated by reference. These results are reported in Table III.

TABLE III

Adsorbent A Characteristics After Alkyl Amine Hydrochloride Exchange

| Exchange Media | 0 | 0 | MA . HCl | MA . HCl | DMA . HCl | DMA . HCl |
|---|---|---|---|---|---|---|
| % Water on Adsorbent | 0 | 4 | 0 | 2 | 0 | 2 |
| p-Xylene Retention Volume, cc | 20.7 | 17.8 | 20.0 | 25.5 | 19.7 | 21.6 |

SELECTIVITIES
Para-Xylene to Other Feed Components

| | | | | | | |
|---|---|---|---|---|---|---|
| pX/EB | 1.49 | 1.47 | 2.48 | 2.04 | 2.28 | 1.88 |
| pX/mX | 4.33 | 4.29 | 4.04 | 4.51 | 4.29 | 4.28 |
| pX/oX | 4.00 | 3.61 | 3.71 | 4.00 | 3.17 | 3.76 |

Para-Xylene to Desorbent

| | | | | | | |
|---|---|---|---|---|---|---|
| pX/p-DEB | — | 0.68 | — | 0.95 | — | — |

EXAMPLE III: SELECTIVITY TESTS

The same tests were performed on Adsorbent B. The results are presented in Table IV presented below.

TABLE IV

Adsorbent B Characteristics After Alkyl Amine Hydrochloride Exchange

| Exchange Media | 0 | 0 | MA . HCl | MA . HCl | DMA . HCl | DMA . HCl |
|---|---|---|---|---|---|---|
| % Water on Adsorbent | 0 | 4 | 0 | 4 | 0 | 4 |
| p-Xylene Retention Volumes, cc | — | 19.7 | 20.9 | 30.08 | 22.0 | 19.9 |

SELECTIVITIES
Para-Xylene to Other Feed Components

| | | | | | | |
|---|---|---|---|---|---|---|
| pX/EB | 2.03 | 1.70 | 2.79 | 1.79 | 2.15 | 1.88 |
| pX/mX | 2.98 | 4.85 | 4.59 | 3.95 | 3.02 | 4.97 |
| pX/oX | 2.66 | 4.40 | 4.43 | 3.79 | 2.59 | 4.61 |

TABLE IV-continued

| | Para-Xylene to Desorbent | | | | |
|---|---|---|---|---|---|
| pX/p-DEB | — | 0.90 | — | 1.30 | — | — |

EXAMPLE IV

Adsorbent C was tested in the same manner. The results are reported in Table V below.

TABLE V

| Adsorbent C Characteristics After Alkyl Amine Hydrochloride Exchange | | | |
|---|---|---|---|
| Exchange Media | 0 | MA . HCl | DMA . HCl |
| % Water on Adsorbent | 4 | 4 | 4 |
| p-Xylene Retention Volumes, cc | 23.7 | 33.6 | 26.9 |
| SELECTIVITIES Para-Xylene to Other Feed Components | | | |
| pX/EB | 1.94 | 1.92 | 1.91 |
| pX/mX | 4.01 | 4.63 | 5.06 |
| pX/oX | 4.64 | 4.55 | 4.61 |
| Para-Xylene to Desorbent | | | |
| pX/p-DEB | 1.15 | 1.30 | — |

EXAMPLE V

Adsorbent D was tested in the same manner. The results are presented in Table VI below.

TABLE VI

| Adsorbent D Characteristics After Alkyl Amine Hydrochloride Exchange | | | |
|---|---|---|---|
| Exchange Media | 0 | MA . HCl | DMA . HCl |
| % Water on Adsorbent | 0 | 0 | 0 |
| p-Xylene Retention Volumes, cc | 20.4 | 37.03 | 26.75 |
| SELECTIVITIES Para-Xylene to Other Feed Components | | | |
| pX/EB | 1.92 | 2.03 | 1.74 |
| pX/mX | 3.52 | 2.64 | 3.29 |
| pX/oX | 3.40 | 2.34 | 2.66 |
| Para-Xylene to Desorbent | | | |
| pX/p-DEB | 0.62 | 1.52 | 1.12 |

DISCUSSION OF RESULTS

The effect of water on adsorbent characteristics before and after alkyl amine treatment was studied. It is preferred to operate with relatively low levels of water on untreated sieves because increased water levels on the sieve tend to decrease the para-xylene to ethylbenzene selectivity of the sieve as well as reducing the overall sieve capacity. The action of water is not completely understood, it is believed to act as a promoter, and improve exchange rates. Operating with less than an optimum amount of water cuts down purity and recovery, so some water maintenance is preferred in commercial units. Operation without water would be preferred because there would be one less variable to be concerned with.

All of the sieves showed an increase in selectivity for para-xylene over ethylbenzene after treatment, with one exception, Adsorbent D, which showed a slight decrease in selectivity when DMA.HCl was used. All of the adsorbents showed enhanced selectivity for para-xylene/p-DEB, with the greatest improvement shown for Adsorbent D, wherein the selectivity changed from 0.62 to 1.52.

The results experienced with Adsorbent A, adsorbent originally designed for operation with toluene, and Adsorbent D are especially significant. Adsorbent A, after treatment with MA.HCl, works as well with p-DEB desorbent as Adsorbent B, which was designed to perform with a p-DEB desorbent. As an additional advantage, Adsorbent A, after treatment, has a somewhat higher pX-EB selectivity than untreated Adsorbent B. This means that a petrochemical manufacturer operating with Adsorbent A can, with an alkyl amine hydrochloride treatment produce an adsorbent which will perform very well using p-DEB desorbent. He can be assured of good performance because the selectivities for para-xylene relative to the other xylenes in ethylbenzene all exceed 2.0, whereas without the alkyl amine hydrochloride treatment, the pX-EB selectivity is an unsatisfactory low 1.49 to 1.47 using p-DEB desorbent. These low selectivities experienced with Adsorbent A, prior to treatment with an alkyl amine hydrochloride, are not indications of deficiencies in the desorbent itself, as the desorbent would function perfectly well if toluene were used as the desorbent rather than the p-DEB used in these tests.

Adsorbent D characteristics are changed markedly by alkyl amine treatment. The ratio of para-xylene to para-diethylbenzene changes from less than one to greater than one (1.1–1.5 being desired) which allows p-DEB to function better as a desorbent. The added advantage is that maintenance of water on the sieve is not necessary. It points to control of the pX/p-DEB ratio by alkyl amine hydrochloride addition to maximize economics of plant operation.

For all the adsorbents tested, the para-xylene retention volume increased. The significance of this change is that effective sieve capacity increases and adsorbent inventory decreases. The optimum amount of alkyl amine hydrochloride used will depend on the unique economics of each unit, and will be a function of utility costs, fractionator capacity, and product purity and volume requirements.

I claim as my invention:

1. In a process for separating aromatic hydrocarbons from a feed containing a mixture of aromatic isomers including para-isomer, which process comprises contacting, at adsorption conditions, said feed with a Type X or Type Y zeolite which has been cation exchanged at exchangeable cationic sites with cations which make the zeolite selective for the para-isomer, to effect the selective adsorption of said para-isomer by said adsorbent, the improvement which comprises utilizing in said process a Type X or Type Y zeolite which has been treated with an alkyl amine hydrochloride or alkyl amines.

2. The process of claim 1 wherein the alkyl amine hydrochloride is methylamine hydrochloride.

3. The process of claim 1 wherein the alkyl amine hydrochloride is dimethylamine hydrochloride.

4. The process of claim 1 wherein the zeolite is treated with alkyl amine hydrochloride by dissolving the alkyl amine hydrochloride in a polar solvent to form an exchange solution, and the exchange solution is passed over the adsorbent.

5. The process of claim 1 wherein the alkyl amine is methylamine.

6. The process of claim 1 wherein the alkyl amine is dimethylamine.

7. The process of claim 1 wherein the zeolite is treated with alkyl amine or derivative thereof by dissolving it in a polar solvent to form an exchange solution, and the exchange solution is passed over the adsorbent.

8. The process of claim 1 wherein from about 0.004 to about 0.121 equivalents of alkyl amine hydrochloride or derivative thereof are added to said zeolite.

* * * * *